(12) United States Patent
Kockx et al.

(10) Patent No.: US 9,968,772 B2
(45) Date of Patent: May 15, 2018

(54) ADAPTOR

(71) Applicant: KONINKLIJKE PHILIPS N.V., Eindhoven (NL)

(72) Inventors: Franciscus Nicolaas Kockx, Tegelen (NL); Johan Anton Hendrikx, Hamont-Achel (BE); Severin Luc Ramses Harvey, Amsterdam (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 216 days.

(21) Appl. No.: 14/894,547

(22) PCT Filed: May 22, 2014

(86) PCT No.: PCT/EP2014/060513
§ 371 (c)(1),
(2) Date: Nov. 30, 2015

(87) PCT Pub. No.: WO2014/195139
PCT Pub. Date: Dec. 11, 2014

(65) Prior Publication Data
US 2016/0121098 A1    May 5, 2016

(30) Foreign Application Priority Data
Jun. 5, 2013    (EP) ..................... 13170550

(51) Int. Cl.
*A61N 1/04* (2006.01)
*H01R 13/506* (2006.01)
*A61B 5/0416* (2006.01)

(52) U.S. Cl.
CPC ......... *A61N 1/0456* (2013.01); *H01R 13/506* (2013.01); *A61B 5/0416* (2013.01); *A61N 1/0492* (2013.01)

(58) Field of Classification Search
CPC .. A61N 1/0492; A61N 1/0456; A61N 1/3752; H01R 13/506; H01R 11/30;
(Continued)

(56) References Cited

U.S. PATENT DOCUMENTS 4,653,503 A * 3/1987 Heath ................. A61B 5/0408
600/391
5,355,883 A   10/1994 Ascher
(Continued)

FOREIGN PATENT DOCUMENTS

EP       0289208 A2    11/1988
EP       1776922 A1    4/2007
WO     2011151742 A1   12/2011

*Primary Examiner* — Edwin A. Leon

(57) ABSTRACT

There is provided an adaptor for forming an electrical connection between a medical device having a first type of connector and an electrode having a second type of connector. The adaptor has a first connecting part shaped to cooperate with a corresponding connecting part on one of the medical device and the electrode so as to form a mechanical and electrical connection therebetween. The adaptor further has a second connecting part having a portion of magnetic or ferromagnetic material arranged to be magnetically attracted to a corresponding magnet or portion of ferromagnetic material included in a magnetic connector part on the other of the medical device and the electrode, so as to form a magnetic and electrical connection therebetween. The first connecting part is electrically connected to the second connecting part.

14 Claims, 4 Drawing Sheets

(58) Field of Classification Search
CPC ............... H01R 13/7037; H01R 13/53; H01R 13/2421; H01R 13/64; H01R 31/06; H01R 13/5224; H01R 24/58; H01R 2201/12; A61B 5/0416; H01F 38/14
USPC .............................. 439/38–39, 909; 607/115
See application file for complete search history.

(56) References Cited

U.S. PATENT DOCUMENTS

| | | |
|---|---|---|
| 6,671,554 B2 | 12/2003 | Gibson |
| 7,993,167 B2 | 8/2011 | Keightley et al. |
| 9,131,895 B2 | 9/2015 | Grob |
| 9,325,107 B2 * | 4/2016 | Karls ................. H01R 13/6205 |
| 2003/0195587 A1 * | 10/2003 | Rigaux ................ A61N 1/0452 |
| | | 607/48 |
| 2009/0227857 A1 | 9/2009 | Rowe et al. |
| 2012/0196474 A1 | 8/2012 | Selvitelli et al. |
| 2013/0023816 A1 | 1/2013 | Bachinski et al. |
| 2013/0066412 A1 | 3/2013 | Van Der Beek et al. |
| 2015/0303619 A1 * | 10/2015 | Kockx ................... A61N 1/048 |
| | | 607/149 |

* cited by examiner

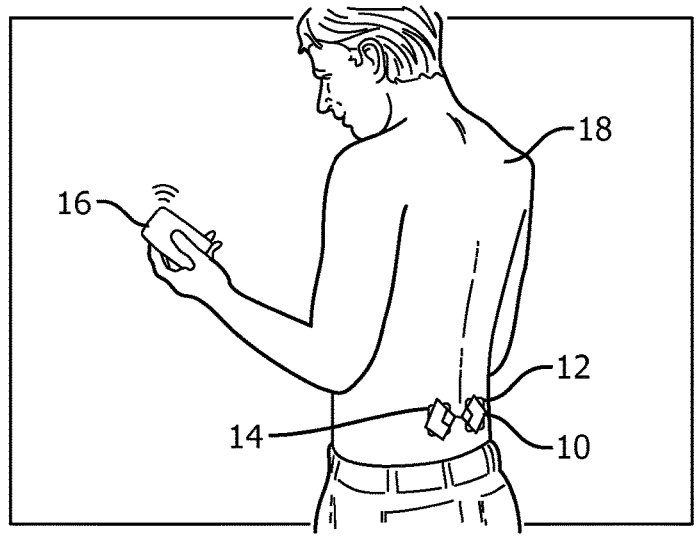
Prior art
FIG. 1
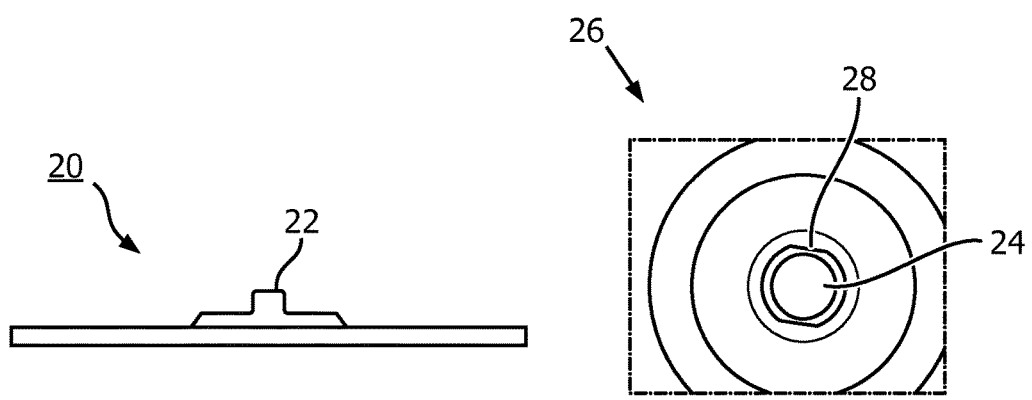
Prior art
FIG. 2a
Prior art
FIG. 2b

ADAPTOR

CROSS-REFERENCE TO PRIOR APPLICATIONS

This application is the U.S. National Phase application under 35 U.S.C. § 371 of International Application No. PCT/EP2014/060513, filed on May 22, 2014, which claims the benefit of European Patent Application No. 13170550.1, filed on Jun. 5, 2013. These applications are hereby incorporated by reference herein.

FIELD OF THE INVENTION

An adaptor for forming an electrical connection between a first device having a first type of connector and a second device having a second type of connector, and in particular relates to an adaptor which forms an electrical connection between a medical device and an electrode for attachment to a subject's body.

BACKGROUND OF THE INVENTION

Physiological electrodes attached to the skin of a subject can receive electrical signals generated by the human body, which are then used to monitor physiological functions (such as heart rate and muscle activity), and/or can deliver electrical signals to the body, for example to stimulate muscle contraction or relieve pain.

For example, transcutaneous electrical nerve stimulation (TENS) is a technique in which electric current is applied to a body part of the subject via two or more skin mounted electrodes. TENS treatment typically requires electrical current to be applied to the body for a significant amount of time each day, including while the subject goes about their daily activities. In wireless TENS, a TENS device (which generates the electrical current in response to a signal from a control unit) is placed directly on an electrode attached to the skin of a subject. FIG. 1 shows a wireless TENS system comprising a TENS device 10 carried by two electrodes 12, 14, and a remote control 16, being used to treat the lower back of a subject 18.

It is a key benefit for a user of a TENS or other electrode-based system to be able to easily connect and disconnect the medical device from the electrode. This facilitates connection to electrodes in difficult to reach body positions (e.g. the back) and on soft tissue areas which do not offer much resistance to a pushing or pulling force. An easy-to-use connector is also necessary for subjects who have reduced use of their hands and fingers (for example because they suffer from osteoarthritis).

Known skin electrodes, including those used for TENS, are typically connected to a medical device (such as a TENS device) using a mechanical connection. One known type of electrode has a lead wire which extends from the top surface of the electrode pad and ends in a female jack connector. This is configured to engage in a push-fit connection with a male jack connector provided on a lead wire extending from a medical device.

Another commonly-used type of electrode 20, shown in FIG. 2a, has a male snap structure 22 configured to engage in a snap-fit connection with a female receiving portion 24 of a medical device connector 26 (shown in FIG. 2b). The snap connection is achieved by cooperation between the shape of the male snap structure 22 and the shape of the female receiving portion 24. In the illustrated example, a metal spring 28 on the receiving portion 24 seats into a recessed portion of male snap structure 22 when the electrode 20 and connector 26 are connected.

The mechanical connection between the male and female structures of the snap connector means that force is required to connect and disconnect the electrodes from the medical device. This makes such connectors difficult to use by people who are unable to easily apply the required amount of force. It also makes connection to electrodes located on soft body parts (such as the stomach) very difficult or impossible, since such body parts do not provide a firm support to press or pull against. It also makes connection to electrodes located on painful body parts (for example which have been injured) unpleasant; since the force which needs to be applied may cause further pain and discomfort. These difficulties of connecting the medical device connector and the electrode may lead to improper connections, reducing the effectiveness of the treatment or monitoring being carried out by means of the medical device.

To mitigate these issues, the use of magnetic connectors to connect medical devices to electrodes has been proposed. WO2011/151742, for example, describes an electrode assembly comprising an electrode and a connector, in which a connection between the electrode and connector is formed by way of a magnet provided in the connector assembly magnetically coupling to a magnet or portion of ferromagnetic material in the electrode.

An example of a magnetic connector/electrode assembly is shown in FIG. 3a. The illustrated medical device 10 has a connector 32 comprising an annular magnet 34. It is connected to an electrode 30 having a circular ferromagnetic metal target 36. The target 36 has a central stud 38 which engages the hole in the annular magnet 34. The cooperation between the stud 38 and the hole prevents relative lateral movement of the electrode 30 and the medical device 10, but does not hinder their separation. Another example of a known magnetic connector/electrode assembly is shown in FIG. 3b. In this example the medical device 10 has a connector 33 which comprises a magnet 35 which protrudes from an outer surface of the medical device 11. It is connected to an electrode 31 having a ferromagnetic metal target 37 with a central recess configured to receive the magnet 35, so that lateral movement between the electrode 31 and the medical device 11 is prevented.

Since electrodes which must be adhered to a patient's skin are typically used just once, or a few times, before being disposed of, TENS patients and medical facilities which make use of electrode-based medical devices must periodically purchase stocks of electrodes. If a patient or medical facility acquires a new medical device which uses a different type of connector, for example a magnetic connector, they also need to purchase a new stock of specialised electrodes adapted for use with this particular type of connector. If they no longer have any devices using the old type of connector, they will also have to discard any remaining of their existing stock of electrodes.

It would therefore be desirable to be able to use conventional, mechanical-connector type electrodes with medical devices that use magnetic connectors, so that the above-described benefits of magnetic connectors can be obtained without the expense of purchasing new stocks of electrodes, or, in the case of a medical facility which uses various types of electrode-based medical devices, the inconvenience of having to maintain stocks of several different types of electrode.

SUMMARY OF THE INVENTION

According to a first aspect of the invention, there is provided an adaptor for forming an electrical connection between a medical device having a first type of connector and an electrode having a second type of connector. The adaptor comprises a first connecting part shaped to cooperate with a corresponding connecting part on one of the medical device and the electrode so as to form a mechanical and electrical connection therebetween; and a second connecting part comprising a portion of magnetic or ferromagnetic material arranged to be magnetically attracted to a corresponding magnet or portion of ferromagnetic material comprised in a magnetic connector part on the other of the medical device and the electrode, so as to form a magnetic and electrical connection therebetween. The first connecting part is electrically connected to the second connecting part.

In order to facilitate the connection and disconnection of a medical device to one or more electrodes, it is desirable to use a magnetic connection between the medical device and the electrodes. However, this must be balanced against the cost and inconvenience to the user of obtaining a new medical device and electrodes, and/or their need to utilise existing stocks of electrodes of a given type. Embodiments of the claimed invention advantageously enable a magnetic connection to be formed between a medical device having a mechanical connector and an electrode having a magnetic connector, thus enabling a user of the medical device to obtain the benefits of a magnetic connection with their existing device. Other embodiments advantageously enable a connection to be formed between a medical device having a magnetic connector and an electrode having a mechanical connector, thus enabling a user who has upgraded their medical device to one with a magnetic connector to use it with their existing stock of mechanical connector electrodes.

The first connecting part may be shaped so as to form a snap connection with the corresponding connecting part. In such embodiments, the first connecting part may comprise a surface having a recess, wherein the recess is shaped to resist the removal from the recess of a protrusion on the corresponding connecting part. The recess may be circular and comprise a spiral spring disposed on its circumference, wherein the spiral spring is biased into a configuration in which the circumference of the spiral spring is less than the maximum circumference of the recess.

The second connecting part may comprise a target having a connection surface configured to abut a corresponding connection surface on the magnetic connector part. In such embodiments, the target may be at least partially formed from a ferromagnetic material. The connection surface may comprises a protrusion extending from the connection surface, the protrusion being configured to be received within a recess on the corresponding connection surface on the magnetic connector part. Advantageously, in embodiments having this feature lateral movement between the second connecting part and the magnetic connector part is prevented without impairing the ease of disconnection of the second connecting part and the magnetic connector part.

The first connecting part may be formed integrally with the second connecting part.

The invention further provides, according to a second aspect, an electrode assembly comprising an electrode configured to form a mechanical connection with a medical device, and an adaptor as described above.

The invention further provides, according to a third aspect, a connector assembly for forming an electrical connection between a medical device and an electrode according to claim 10. The assembly comprises an adaptor as described above; a magnetic connector part disposed on one of the medical device or the electrode and arranged to be magnetically attracted to the portion of magnetic or ferromagnetic material in the second connecting part of the adaptor; and a mechanical connector part disposed on the other of the medical device or the electrode, and shaped to cooperate with the first connecting part of the adaptor.

The magnetic connector part may be disposed on the medical device and the mechanical connector part may be is disposed on the electrode. In such embodiments, the magnetic connector part may comprise a magnet and the second connecting part may comprise a portion of ferromagnetic material.

The mechanical connector part may comprise a female pin connector and the first connecting part may comprise a male pin connector. The first connecting part may comprise a lead wire electrically connected at one end to the second connecting part and at the other end to a connecting means. The electrode may comprise a lead wire electrically connected at one end to a portion for attachment to a user and at the other end to the female pin connector.

BRIEF DESCRIPTION OF THE DRAWINGS

For a better understanding of the invention, and to show more clearly how it may be carried into effect, reference will now be made, by way of example only, to the accompanying drawings, in which:

FIG. 1 shows a prior art TENS system in use;

FIG. 2a is a cross-section through a prior art electrode connected to a prior art medical device by a snap connection;

FIG. 2b shows a prior art medical device snap connector;

DETAILED DESCRIPTION OF EMBODIMENTS

Figure 3A:
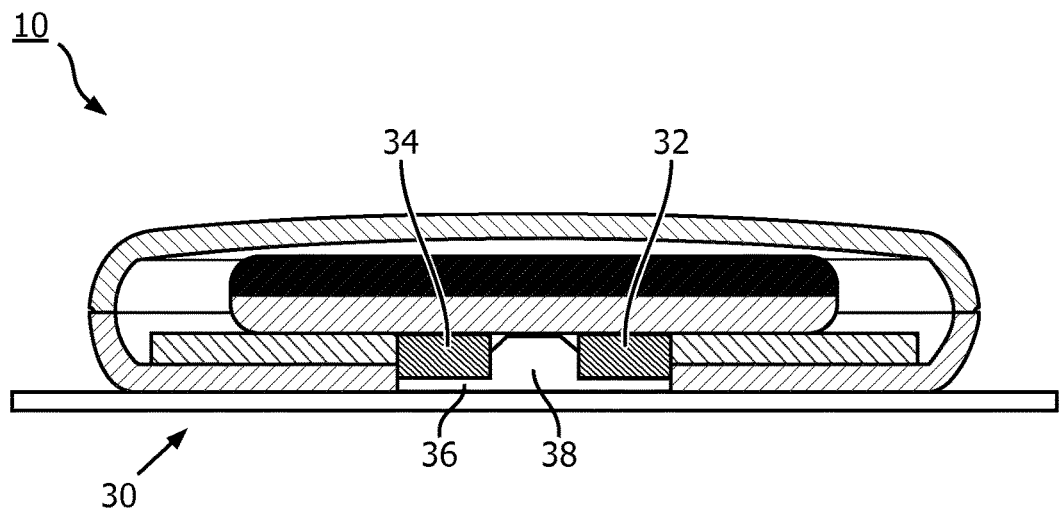
FIG. 3a is a cross-section through a first exemplary prior art electrode connected to a prior art medical device by a magnetic connection.
Figure 3B:
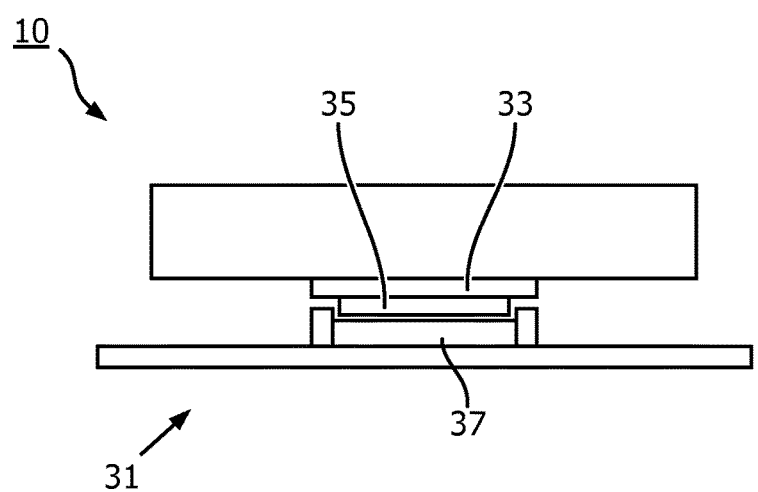
FIG. 3b is a cross-section through a second exemplary prior art electrode connected to a prior art medical device by a magnetic connection.
Figure 4:
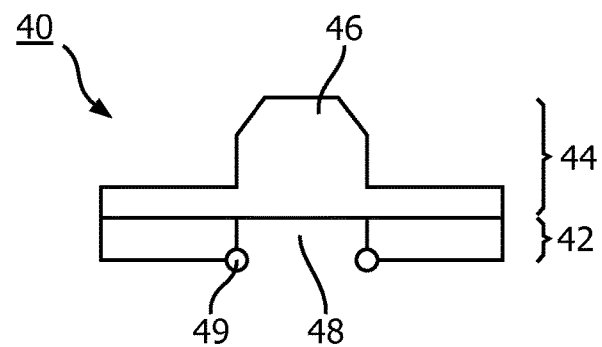
FIG. 4 is a cross-section through an adaptor according to an embodiment of the invention.

FIG. 4 shows an adaptor 40 for forming an electrical connection between a medical device (not shown) having a first type of connector and an electrode (not shown) having a second type of connector according to embodiments of the invention. The adaptor 40 comprises a first connecting part 42 shaped to cooperate with a corresponding connecting part on one of the medical device and the electrode so as to form a mechanical and electrical connection therebetween. The adaptor 40 further comprises a second connecting part 44. The second connecting part 44 comprises a portion of magnetic or ferromagnetic material arranged to be magnetically attracted to a corresponding portion of magnetic or ferromagnetic material in a magnetic connector part on the other of the medical device and the electrode, so as to form a magnetic and electrical connection therebetween.

The first connecting part 42 of the adaptor 40 shown in FIG. 4 is a snap connector. In the illustrated example, the snap connector is a female snap connector comprising a circular recess 48 having a spiral spring 49 at its rim. The spiral spring 49 is biased into a configuration in which its circumference is smaller than the circumference of the recess. The spiral spring 49 can expand its circumference to allow a corresponding connecting part in the form of a cooperatively shaped male snap connector portion to enter the recess. The spiral spring 49 can then contract to engage with a formation, for example a circumferential indentation, on the male snap connector portion. This engagement forms a mechanical connection which resists separation of the first connecting part 42 and the corresponding connector part. Although FIG. 4 shows the first connecting part 42 as a female snap connector having a recess and a spiral spring, it will be appreciated that the first connecting part may comprise a male snap connector, or indeed may be formed in any way known in the art suitable for forming a mechanical connection with a correspondingly shaped connecting part.

The second connecting part 44 of the adaptor 40 shown in FIG. 4 comprises a target 46 formed from a ferromagnetic material. The top surface of the target 46 forms a connection surface which is arranged to abut a corresponding connection surface of a magnetic connector part, and thereby to form an electrical connection with that magnetic connector part. A protrusion extends from the connection surface of the target 46. This protrusion is shaped so as to engage with a corresponding recess in the connection surface of the magnetic connector part so as to prevent lateral movement between the magnetic connector part and the second connecting part 44. In alternative embodiments, the connection surface of the second connecting part 44 comprises a recess for engaging with a corresponding protrusion on a connection surface of a magnetic connector part.

Preferably the protrusion is arranged so as to permit relative rotation therebetween when the adaptor 40 is connected to a corresponding magnetic connector part. Permitting relative rotation between the adaptor and a corresponding magnetic connector part to which it is connected helps to ensure that the user's freedom of movement is not restricted when using the adaptor 40 to wear a TENS device. This is also advantageous in other situations, including for example when the adaptor is used to form a connection between a muscle stimulation device and skin-mounted electrodes during physical therapy. Cooperation between the protrusion and a corresponding recess also has an advantage in facilitating easier location and coupling of the adapter 40 with a corresponding magnetic connector part. Preferably the protrusion comprises a stud.

Preferably the target 46 comprises an electrically conductive ferromagnetic material, such as a ferromagnetic metal. Alternatively, however, the target could comprise a non-electrically conductive ferromagnetic material coated with an electrically conductive material. In some alternative embodiments the target 46 comprises a magnetic material. It will be appreciated that adaptors 40 according to such embodiments are capable of forming a magnetic connection with corresponding magnetic connector parts which include ferromagnetic material but do not comprise a magnet. Preferably the surface area of the target 46 is substantially the same size and shape as the connection surface of the magnetic connector part to which the adaptor is intended to be connected.

The first connecting part 42 is joined to the second connecting part 44 such that electrical signals may pass between the first and second connecting parts 42, 44. This joining may be effected by any suitable means known in the art, including (but not limited to) welding, riveting or use of an adhesive layer. Alternatively, the first and second connecting parts 42, 44 may be joined by a lead wire or may have a lead wire or wires passing through each of the conducting parts 42, 44. The mechanical strength of the connection formed by the join between the first and second connecting parts 42, 44 is preferably significantly stronger than the strength of the mechanical connection formed between the first connecting part 42 and a corresponding connecting part, and than the strength of the magnetic connection formed between the second connecting part 44 and a corresponding connecting part, so as to minimise the risk of the two connecting parts 42, 44 separating during use of the adaptor. In some embodiments the first and second connecting parts 42, 44 are formed integrally, in which case there is no risk of separation.

Figure 5:
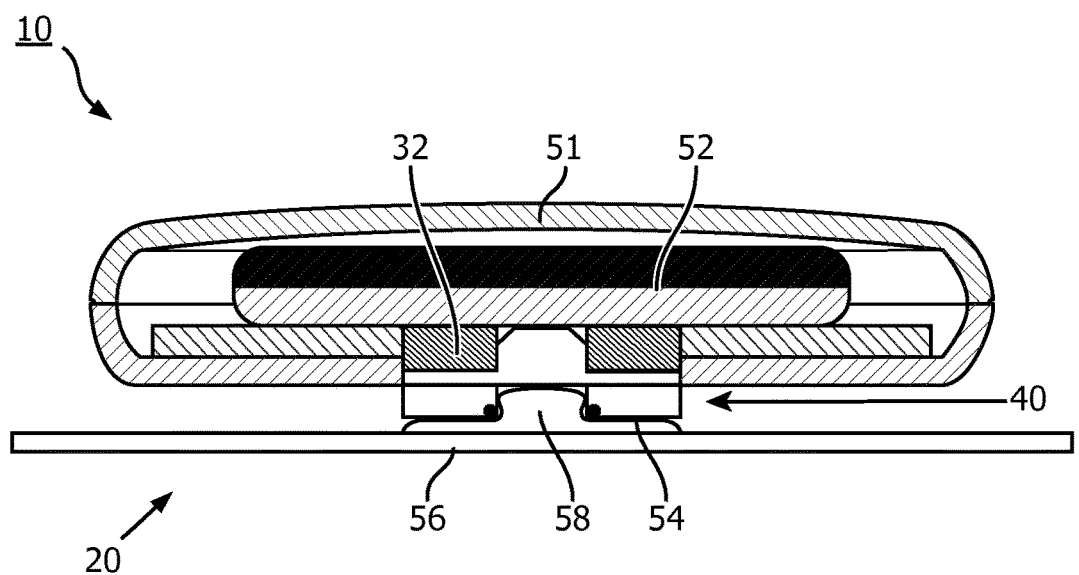
FIG. 5 is a cross-section through the adaptor of FIG. 4, connected to a prior art medical device and a prior art electrode.

FIG. 5 shows the adaptor 40 connected to a medical device 10 and to an electrode 20. The illustrated medical device 10 is a wireless TENS device and the illustrated electrode 20 is an adhesive skin patch electrode, although it will be appreciated that the adaptor 40 can be used with any medical device arranged to connect to one or more electrodes of any type, and indeed with any system in which a first component needs to be mechanically and electrically coupled to a second component.

The medical device 10 has a housing 51 containing a package of electronic components 52 for generating an electrical current, including a battery and a receiver for receiving control signals from a remote control. The housing 51 also comprises a magnetic connector part 32. The magnetic connector part 32 is electrically connected to the electronic components 52 by means of a lead, solder connection or any other suitable way of making an electronic connection known to the skilled person, such that an electronic signal generated by the electronic components 52 is transmitted to the magnetic connector part 32. On an outer surface of medical device 10 the housing 51 includes a hole sized to accommodate the magnetic connector part 32, such that the outer surface of magnetic connector part 32 forms part of the outer surface of device 10. The outer surface of magnetic connector part 32 is arranged to abut the connection surface of the second connecting part 44 of the adaptor 40 and thereby to form an electrical connection with the second connecting part 44.

The magnetic connector part 32 comprises a magnet 34. The illustrated magnet is annular, although it will be appreciated that other arrangements of one or more magnets of any suitable shape could equally be used. Magnet 34 comprises any suitable magnetic material known in the art, for example neodymium. The magnet 34 may be coated with a layer of electrically conducting material such as nickel. The connection surface of the magnetic connector part 32 includes a recess corresponding to the central hole of magnet 34. This recess can accommodate a protrusion extending from a corresponding connecting part, for example the stud on the second connecting part 44 of the adaptor 40. In alternative embodiments the connection surface of the magnetic connector part 32 is flat. In still other embodiments the connection surface of the magnetic connector part 32 comprises a protrusion, in which case the connection surface of the second connecting part 44 comprises a recess suitable for receiving this protrusion.

The illustrated electrode 20 comprises an electrically conductive target 54 attached to a layer of flexible material 56 by any suitable attachment means known in the art, for example a pin which passes through layer of flexible material 56 and engages with target 54. The target 54 may be formed from any suitable material known to the skilled person, for example metal. The layer of flexible material 56 may comprise any suitable material, for example a fabric or a plastics material. If the material forming the layer of flexible material is not electrically conductive, then conducting means are provided to transmit electrical signals through this layer. An adhesive layer (not shown) is provided on the bottom surface of the layer of flexible material 56 to facilitate attachment to skin.

A protrusion 58 extends from the top surface of the target 54. The protrusion 58 is shaped to mechanically engage with a formation provided on corresponding connecting part so as to resist separation of the target from the corresponding connecting part once a connection has been formed. In the illustrated embodiment this is achieved by the protrusion 58 comprising a stud having a larger diameter at its distal end than at its base. It will be appreciated that in alternative embodiments the target 54 can comprise a formation for engaging a protrusion, in which case the first connecting part 42 will comprise a suitable protrusion. Indeed, the target may be formed in any way known in the art suitable for forming a mechanical connection with a correspondingly shaped connecting part.

Figure 6A:
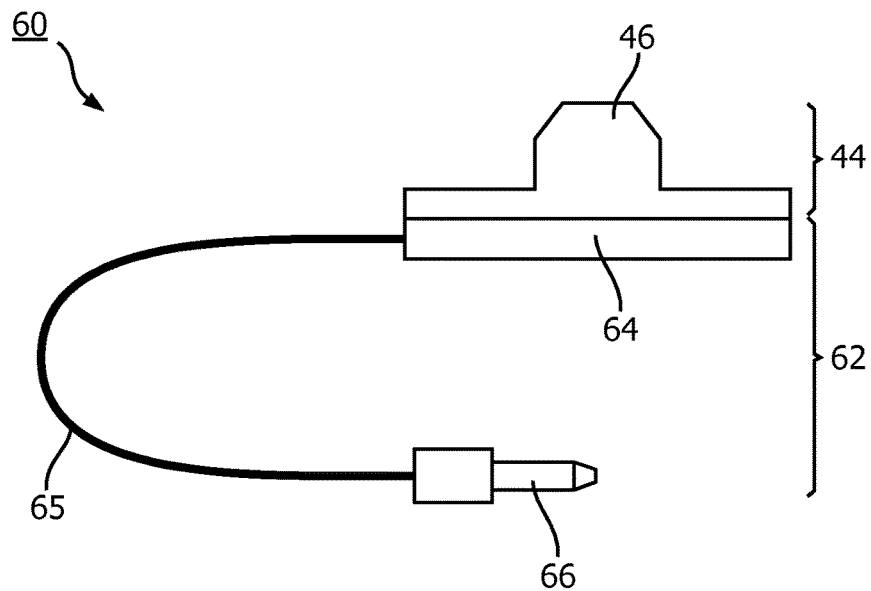
FIG. 6a shows an adaptor according to a first alternative embodiment of the invention.
Figure 6B:
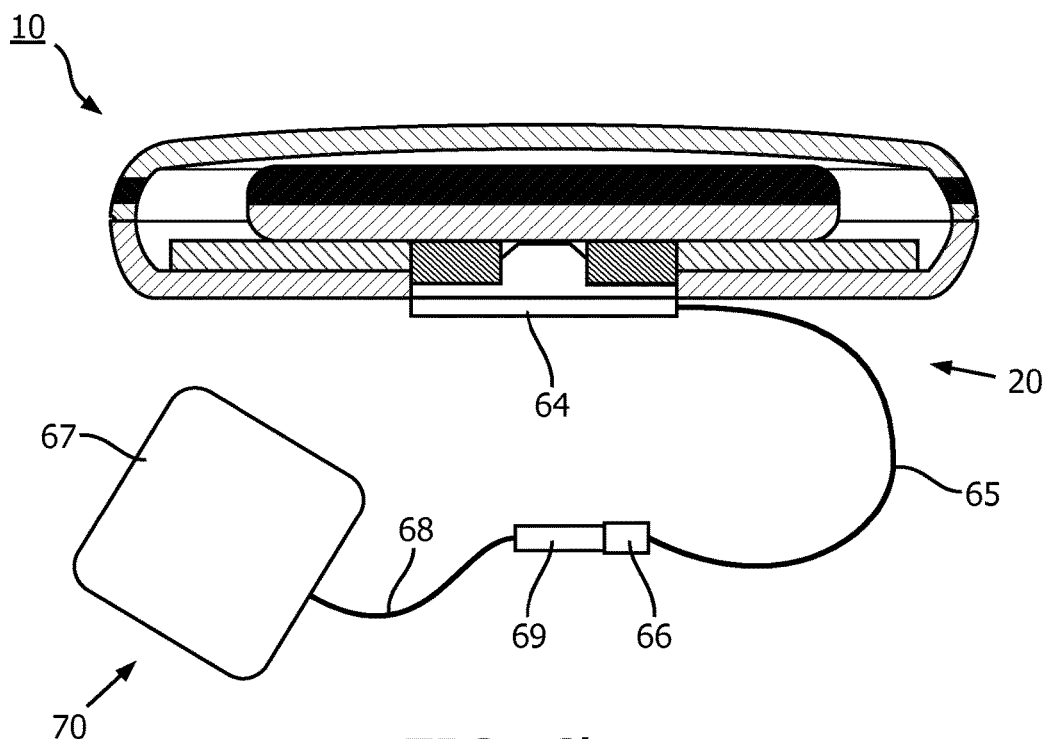
FIG. 6b shows the adaptor of FIG. 6a, connected to a prior art medical device and a prior art electrode.

FIGS. 6a and 6b show a first alternative embodiment in which an adaptor 60 comprises a second connecting part 44 as described above, joined to a first connecting part 62 which is arranged to connect to an electrode 70 via a lead wire. The first connecting part 62 comprises an electrically conductive plate 64. A lead wire 65 is electrically connected to the plate 64 and extends outwardly from one side of the plate 64. A male pin connector 66 is provided at the distal end of the lead wire 65 for forming a mechanical and electrical connection with a female pin connector of an electrode. It is advantageous for the lead wire 65 to end with a male pin connector because conventional pin connection electrodes are typically provided with a lead wire ending in a female pin connector. However, it will be appreciated that lead wire 65 could equally be provided with a female pin connector, or with any other type of connector suitable for forming a mechanical and electrical connection. In some embodiments the lead wire 65 can be provided with a connector arranged to connect to a corresponding connector which is not on a lead wire. For example, lead wire 65 may terminate in a male or female snap connector.

In FIG. 6b the adaptor 60 is shown connected to the medical device 10 and to an electrode 70. The connection between the adaptor 60 and the medical device 10 is formed via the first connecting part 44 of the adaptor 60 in the same manner as described above in relation to the first embodiment. The illustrated electrode 70 is a disposable skin patch electrode with a lead wire ending in a pin connector, although it will be appreciated that the adaptor 70 can be used with any electrode comprising a lead wire, and indeed also with any electrode not comprising a lead wire, by providing the appropriate type of connector on lead wire 65.

Lead wire electrode 70 comprises a layer of flexible material 67, for example a fabric or plastics material. The layer 67 is attached to a lead wire 68 for transmitting electrical signals by any suitable attachment means known in the art. For example, an end of the lead wire 68 may be sandwiched between the layer 67 and a further layer of flexible material, with the sandwich being held together by an adhesive layer. The connection between the lead wire 68 and the layer 67 is such that electrical signals can be transmitted from the lead wire 68 to the layer 67, and from there to a user's skin. If the material forming the layer of flexible material 67 is not electrically conductive, then conducting means are provided to transmit electrical signals through this layer. An adhesive layer (not shown) is provided on the bottom surface of the layer of flexible material 67 to facilitate its attachment to skin. The distal end of lead wire 68 is provided with a female pin connector 69, although it will be appreciated that any other suitable lead wire connector may be provided instead. It will further be appreciated that the type of connector 66 provided on the lead wire 65 of adaptor 60 will be chosen so as to be suitable for forming a mechanical and electrical connection with the particular type of connector used by the electrode with which it is desired to form a connection.

In use, an adaptor 40, 60 according to embodiments of the invention is preferably connected to an electrode 20, 70 before the electrode is applied to the skin of a user. This means that the mechanical connection (the formation of which typically requires a mechanical force to be applied to the adaptor and/or the electrode) between the adaptor 40, 60 and the electrode 20, 70 may be formed without difficulty or discomfort for the user even if they are injured and/or have limited use of their hands, for instance by using a hard table surface to provide support. It will be appreciated, however, that the adaptor 40, 60 may if desired be connected to an electrode 20, 70 after that electrode has been applied to the skin of the user.

When the connected adaptor 40, 60 and electrode 20, 70 combination has been applied to the user, the medical device 10 is connected to the adaptor 40, 60 by forming a magnetic connection between the second connecting part 44 of the adaptor and the magnetic connector part 32 of the medical device. An attractive magnetic force will be felt between the magnetic connector part 32 and the second connecting part 44 when the medical device 10 is sufficiently close to the adaptor 40, 60, which aids the user in making the connection. Since the user need not exert any force on the electrode or medical device in order to form the magnetic connection, it is easy for them to connect the medical device 10 to the adaptor 40, 60 and thereby to the electrode 20, 70, even if the electrode is located in a difficult to reach place, on soft and/or painful body tissue, and/or the user has limited use of their hands. By use of the adaptor, these advantages of a magnetic connection can be gained with conventional electrodes designed for use with mechanical connectors. Advantageously, this obviates the need for a user to also obtain specialized electrodes when they acquire a medical device having a magnetic connector.

Alternatively, it allows the user to gain the benefits of a magnetic connection even if they have a device which uses a mechanical connector. This can be achieved, for example, by the user obtaining electrodes with magnetic connectors and using an adaptor according to the invention to connect these electrodes to the mechanical connector part of the device. The magnetic connection between the electrode and adaptor will have the advantageous properties described above, particularly if the user connects the adaptor to the medical device before attempting to make a connection with an electrode, and then subsequently connects the connected medical device and adaptor combination to the electrode effectively as a single unit.

To remove the medical device 10 from an electrode 20, 70, the user must exert a pulling force on the medical device which is sufficient to overcome the magnetic attraction between the magnetic connector part 34 on the medical device 10 and the second connecting part 44 on the adaptor 40, 60; or which is sufficient to overcome the mechanical force resisting separation of the mechanical connection formed between the first connecting part 42 on the adaptor and the corresponding connector part on the electrode 20, 70. Preferably the force required to separate the magnetic connection is less than the force required to separate the mechanical connection, such that when a user exerts a progressive pulling force on the medical device 10, the medical device is detached from the adaptor 40, 60 whilst the adaptor remains connected to the electrode 20, 70. It will be appreciated that it is possible to arrange the adaptor such that the force required to separate the magnetic connection is equal to or greater than the force required to separate the mechanical connection (for example by adjusting the size and/or material of the portion of magnetic or ferromagnetic material in the second connecting part 44, and/or the nature/adjustment of the mechanism by which the first connecting part 42, 62 engages a corresponding connector part), although such embodiments are less preferred. If the adaptor 40, 60 remains connected to the electrode 20, 70 after detachment of the medical device 10, preferably the adaptor 40, 60 and electrode 20, 70 are removed from the user's skin together using any suitable skin electrode removal method known in the art.

Although the embodiments described above assume that the first (mechanical) connecting part is to be attached to an electrode and the second (magnetic) connecting part is to be attached to the medical device, it will be appreciated that this arrangement may be reversed. However, for many applications it is common practice for the electrodes to be disposable. It is therefore desirable that the construction of the electrodes is as simple and inexpensive as possible, and indeed the user will typically want to purchase the least expensive type of electrode that can be connected to their medical device. Since magnetic connectors are typically more expensive than conventional mechanical connectors, it is envisaged that most users will wish to connect electrodes having conventional mechanical connectors to a medical device having a magnetic connector. The invention is equally applicable, however, in the situation where a user wishes to connect a medical device having a conventional mechanical connector to an electrode having a magnetic connector, for example to gain the benefits of a magnetic connection over a mechanical connection which are described above. For such applications it is advantageous for the second connecting part of the adaptor to comprise a portion of magnetic material, for connection to a ferromagnetic target on an electrode, since the magnetic connector parts typically provided on electrodes do not include magnets for reasons of economy.

It is noted that the various configurations of the first connecting part and the second connecting part of the adaptor may be used in any combination.

Although the invention has been described above as being preferably for use in connecting a wireless TENS device to electrodes mounted on the skin of a subject, it will be appreciated that the invention can advantageously be used with any type medical device which uses electrodes. For example, an adaptor according to the invention could be used with a device for monitoring physiological parameters such as heart rate, or electrical activity in a particular body part, or with a device with delivers stimulation, including devices for stimulating muscles and or nerves, or for transcranial magnetic stimulation. An adaptor according to the invention may also be used with a device for delivering light therapy to a body part. The two electrically connectable components may be a battery and a wearable light therapy device. The light therapy device may be controlled such that the intensity of the LEDs, the period of illumination and/or the grouping of LEDs can be adjusted to provide a sequential light therapy effect. The light therapy device may comprise LEDs emitting a single wavelength or a combination LEDs emitting differing wavelengths, these wavelengths may be applied to the body part individually or simultaneously. The light therapy device may also comprise time control, this control may be for all of the LEDs within the light therapy device, a single LED or a group of LEDs. Light therapy may be used to provide relief from and/or to treat skin conditions such as for example, psoriasis and eczema. Light therapy may also be used to provide relief from pain. The invention could also be used in applications where the medical device is to be connected to an electrode that is at least partially implanted into the subject. Although the invention is primarily concerned with medical applications, it will be appreciated that the invention can advantageously be used in any application where it is desired to form an electrical connection between two electronically connectable components, one of which has a magnetic connector part and the other of which has a mechanical connector part.

There is therefore provided an adaptor for forming an electrical connection between a first device having a first type of connector and a second device having a second type of connector.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An adaptor for forming an electrical connection between a medical device having a first type of connector and an electrode having a second type of connector, the adaptor comprising:
    a first connecting part shaped to cooperate with a corresponding connecting part on one of the medical device and the electrode so as to form a mechanical and electrical connection therebetween; and
    a second connecting part comprising a portion of magnetic or ferromagnetic material arranged to be magnetically attracted to a corresponding magnet or portion of ferromagnetic material comprised in a magnetic connector part on the other of the medical device and the electrode, so as to form a magnetic and electrical connection therebetween;
    wherein the first connecting part is electrically connected to the second connecting part.

2. An adaptor according to claim 1, wherein the first connecting part is shaped so as to form a snap connection with the corresponding connecting part.

3. An adaptor according to claim 2, wherein the first connecting part comprises a surface having a recess, wherein the recess is shaped to resist the removal from the recess of a protrusion, on the corresponding connecting part.

4. An adaptor according to claim 2, wherein the recess is circular and comprises a spiral spring disposed on its circumference, wherein the spiral spring is biased into a configuration in which the circumference of the spiral spring is less than the maximum circumference of the recess.

5. An adaptor according to claim 1, wherein the second connecting part comprises a target having a connection surface configured to about a corresponding connection surface on the magnetic connector part.

6. An adaptor according to claim 5, wherein the target is at least partially formed from a ferromagnetic material.

7. An adaptor according to claim 5, wherein the connection surface comprises a protrusion extending from the connection surface, the protrusion being configured to be received within a recess on the corresponding connection surface on the magnetic connector part.

8. An adapter according to claim 1, wherein the first connecting part is formed integrally with the second connecting part.

9. An electrode assembly comprising:
an electrode configured to form a mechanical connection with a medical device; and
an adaptor including
a first connecting part shaped to cooperate with corresponding connecting part on one of the medical device and the electrode so as to form a mechanical and electrical connection therebetween, and
a second connecting part comprising a portion of magnetic or ferromagnetic material arrange to be magnetically attracted to a corresponding magnet or portion of ferromagnetic material comprised in a magnetic connector part on the other of the medical device and the electrode, so as to form a magnetic and electrical connection therebetween,
wherein the first connecting part is electrically connected to the second connecting part.

10. A connector assembly for forming an electrical connection between a medical device and an electrode, the connector assembly comprising:
an adaptor including a first connecting part and a second connecting part,
wherein the first connecting part is electrically connected to the second connecting part;
wherein the medical device includes one of
i. a magnetic connector part arranged to be magnetically attracted to the portion of magnetic or ferromagnetic material in the second connecting part of the adaptor, or
ii. a mechanical connector part shaped to cooperate with the first connecting part of the adaptor; and
wherein the electrode includes the corresponding other of
i. the mechanical connector part shaped to cooperate with the first connecting part of the adaptor, or
ii. the magnetic connector part arranged to be magnetically attracted to the portion of magnetic or ferromagnetic material in the second connecting part of the adaptor.

11. A connector assembly according to claim 10, wherein the magnetic connector part comprises a magnet and the second connecting part comprises a portion of ferromagnetic material.

12. A connector assembly according to claim 10, wherein the mechanical connector part comprises a female pin connector and the first connecting part comprises a male pin connector.

13. A connector assembly according to claim 10, wherein the first connecting part comprises a lead wire electrically connected at one end to the second connecting part and at the other end to a connecting means.

14. A connector assembly according to claim 12, wherein the electrode comprises a lead wire electrically connected at one end to a portion for attachment to a user and at the other end to the female pin connector.

\* \* \* \* \*